United States Patent
Kanbara et al.

(10) Patent No.: US 9,458,116 B2
(45) Date of Patent: Oct. 4, 2016

(54) BENZOGUANAMINE COMPOUND HAVING AMINOMETHYL GROUP, OR SALT THEREOF, AND METHOD FOR MANUFACTURING THE SAME

(71) Applicant: MITSUBISHI GAS CHEMICAL COMPANY, INC., Chiyoda-ku (JP)

(72) Inventors: Yutaka Kanbara, Niigata (JP); Tomoo Tsujimoto, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 14/909,632

(22) PCT Filed: Jul. 8, 2014

(86) PCT No.: PCT/JP2014/068186
§ 371 (c)(1),
(2) Date: Feb. 2, 2016

(87) PCT Pub. No.: WO2015/019777
PCT Pub. Date: Feb. 12, 2015

(65) Prior Publication Data
US 2016/0176827 A1   Jun. 23, 2016

(30) Foreign Application Priority Data
Aug. 5, 2013 (JP) ................... 2013-162021

(51) Int. Cl.
C07D 251/48 (2006.01)
C07B 31/00 (2006.01)

(52) U.S. Cl.
CPC .................. *C07D 251/48* (2013.01)

(58) Field of Classification Search
CPC .................................... C07D 251/48
USPC ................................ 544/205, 206
See application file for complete search history.

(56) References Cited

FOREIGN PATENT DOCUMENTS

| JP | 61-233013 A | 10/1986 |
|---|---|---|
| JP | 03-200249 A | 9/1991 |
| JP | 03-256048 A | 11/1991 |
| JP | 03-284675 A | 12/1991 |
| JP | 05-202007 A | 8/1993 |
| JP | 07-010850 A | 1/1995 |
| JP | 07-010871 A | 1/1995 |

OTHER PUBLICATIONS

"Sosetsu Epoxy Jushi Kisohen I", The Japan Society of Epoxy Resin Technology, Nov. 19, 2003, (5 pages).
"Epoxy Jushi no Kokazai", ThreeBond Technical News, No. 32, Dec. 20, 1990, http.//www.threebond.co.jp/ja/technical/technicalnews/pdf/tech32.pdf, (10 pages).
International Search Report issued on Sep. 2, 2014 for PCT/JP2014/068186 filed Jul. 8, 2014.

*Primary Examiner* — Venkataraman Balasubramanian
(74) *Attorney, Agent, or Firm* — Oblon, McClelland, Maier & Neustadt, L.L.P.

(57) ABSTRACT

A benzoguanamine compound having an amino methyl group is represented by the following Formula (1), or a salt thereof:

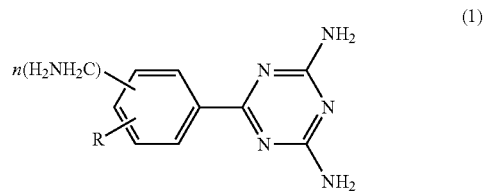

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom, and n is an integer of 1 to 2.

5 Claims, 15 Drawing Sheets

BENZOGUANAMINE COMPOUND HAVING AMINOMETHYL GROUP, OR SALT THEREOF, AND METHOD FOR MANUFACTURING THE SAME

TECHNICAL FIELD

The present invention relates to a benzoguanamine compound having an aminomethyl group, or a salt thereof, and a method for manufacturing the same.

BACKGROUND ART

A benzoguanamine compound is an important raw material for thermosetting resins having excellent properties in terms of compatibility with an oil-soluble resin, water resistance, chemical resistance, heat resistance, surface gloss, electrical properties, stain resistance, and crack resistance. Such thermosetting resins are used as thickeners for coating materials, molding resins, decorative boards, resins for processing fiber and paper, adhesives, and heat-resistant lubricants. Also, a benzoguanamine compound is an important compound for organic synthetic chemistry, as a raw material for polyamide and an additive for increasing flame retardance, and as an agent for preventing resist peeling, a UV ray absorber, or a raw material for medical drugs. Many types of guanamine are conventionally known (refer to Patent Literature 1 to 5).

CITATION LIST

Patent Literature

Patent Literature 1: Japanese Patent Laid-Open No. H07-10871
Patent Literature 2: Japanese Patent Laid-Open No. H05-202007
Patent Literature 3: Japanese Patent Laid-Open No. H07-10850
Patent Literature 4: Japanese Patent Laid-Open No. H03-256048
Patent Literature 5: Japanese Patent Laid-Open No. H03-200249

SUMMARY OF INVENTION

Technical Problem

A benzoguanamine compound having an aminomethyl group in the benzene ring, or a salt thereof is, however, not known. A benzoguanamine compound having an aminomethyl group in the benzene ring, or a salt thereof is expected to be an important compound as a raw material of thermosetting resins in organic synthetic chemistry.

The present invention has been made in view of the above problem. An object of the present invention is to provide a new benzoguanamine compound having an aminomethyl group, or a salt thereof, or an industrially advantageous method for manufacturing a benzoguanamine compound or a salt thereof.

Solution to Problem

The present inventors have performed extensive investigations to solve the problem. As a result, it was found that a benzoguanamine compound having an aminomethyl group, or a salt thereof can be manufactured by hydrogen reduction of cyanobenzoguanamine, or by reaction between aminomethylbenzonitrile and dicyandiamide, and have completed the present invention.

Namely, the present invention is as follows.

[1]

A benzoguanamine compound having an amino methyl group represented by the following Formula (1), or a salt thereof:

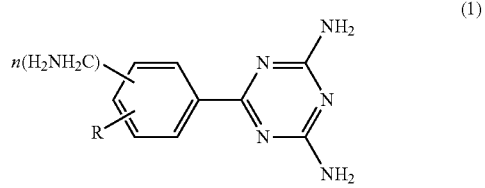

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom, and n is an integer of 1 to 2.

[2]

The benzoguanamine compound having an amino methyl group, or the salt thereof according to the previous section [1], comprising o-aminomethylbenzoguanamine, m-aminomethylbenzoguanamine, or p-aminomethylbenzoguanamine, or a salt thereof.

[3]

A method for manufacturing a benzoguanamine compound having an amino methyl group, or a salt thereof comprising:

a reduction step for obtaining the benzoguanamine compound represented by the following Formula (1) having an aminomethyl group, or the salt thereof by hydrogen reduction of a cyanobenzoguanamine compound represented by the following Formula (2), or a salt thereof in the presence of a catalyst and a solvent:

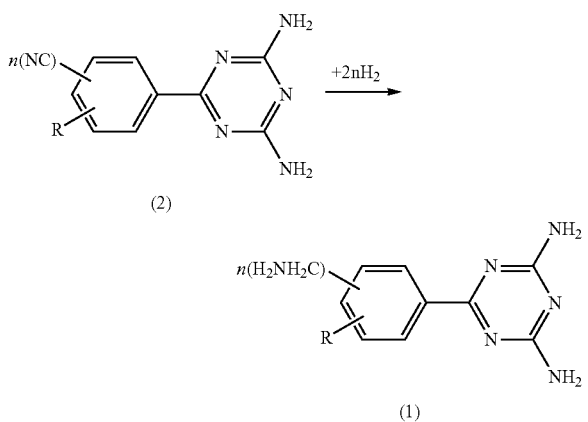

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.

[4]

The method for manufacturing the benzoguanamine compound having an amino methyl group or a salt thereof according to the previous section [3], wherein the catalyst comprises a sponge metal catalyst.

[5]

A method for manufacturing a benzoguanamine compound having an amino methyl group, or a salt thereof comprising:

a reaction step for obtaining the benzoguanamine compound represented by the following Formula (1) having an aminomethyl group by reacting an aminomethylbenzonitrile compound represented by the following Formula (3), or a salt thereof with a dicyandiamide compound represented by the following Formula (4), or a salt thereof:

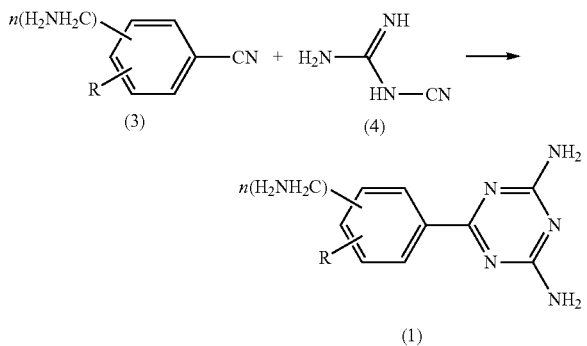

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.

Advantageous Effect of Invention

The present invention can provide a new benzoguanamine compound having an aminomethyl group, or a salt thereof, and an industrially advantageous method for manufacturing a benzoguanamine compound or a salt thereof.

DESCRIPTION OF EMBODIMENT

Figure 1:
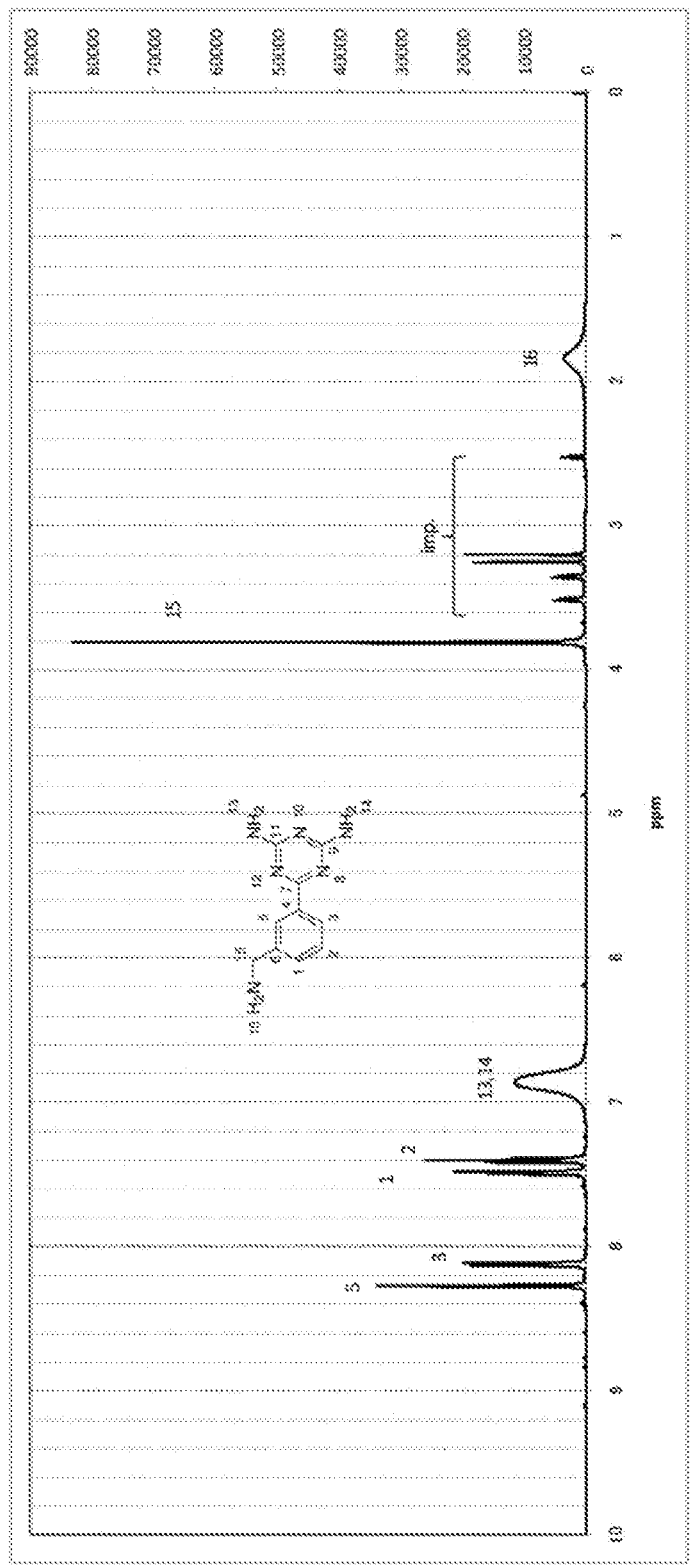
FIG. 1 shows a $^1$H-NMR chart of m-aminomethylbenzoguanamine.

Embodiments of the present invention (hereinafter, referred to as "the present embodiment") are described in detail below, though the present invention is not limited thereto. Various modifications may be made in the present invention within a range not departing from the spirit thereof.

[Benzoguanamine Compound Having Aminomethyl Group, or Salt Thereof]

The benzoguanamine compound having an aminomethyl group, or a salt thereof in the present embodiment is represented by the following Formula (1).

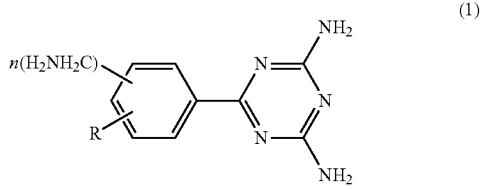

(In the Formula (1), R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom, and n is an integer of 1 to 2.)

In the Formula (1), examples of the alkyl group having 1 to 10 carbon atoms represented by R include a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group, though not particularly limited.

In the Formula (1), examples of the alkoxy group having 1 to 10 carbon atoms represented by R include a methoxy group, an ethoxy group, a linear or branched propoxy group, a linear or branched butoxy group, and a cyclic cyclohexyloxy group, though not particularly limited.

In the Formula (1), examples of the aryl group having 6 to 10 carbon atoms represented by R include a phenyl group and a benzyl group, though not particularly limited.

In the Formula (1), examples of the aryloxy group having 6 to 10 carbon atoms represented by R include a phenoxy group, though not particularly limited.

In the Formula (1), examples of the halogen atom represented by R include a chlorine atom, a fluorine atom and a bromine atom.

Examples of the benzoguanamine compound having an aminomethyl group or a salt thereof in the present embodiment include o-aminomethylbenzoguanamine, m-aminomethylbenzoguanamine, p-aminomethylbenzoguanamine, 3,5-bis(aminomethyl)benzoguanamine, 3,4-bis(aminomethyl)benzoguanamine, 2,5-dimethyl-4-aminomethylbenzoguanamine, or a salt thereof, though not particularly limited.

Examples of the salt of the benzoguanamine compound having an aminomethyl group include a salt of a benzoguanamine compound with an inorganic and/or organic acid, though not particularly limited. In particular, the salt of a cyanobenzoguanamine compound with any one of hydrochloric acid, carbonic acid, and acetic acid is preferred.

[Method for Manufacturing Benzoguanamine Compound Having Aminomethyl Group, or Salt Thereof]

The benzoguanamine compound having an aminomethyl group, or a salt thereof in the present embodiment may be manufactured by a manufacturing method 1 or a manufacturing method 2. The manufacturing method 1 includes a reduction step for obtaining the benzoguanamine compound represented by the following Formula (1) having an aminomethyl group, or a salt thereof by hydrogen reduction of a cyanobenzoguanamine compound represented by the following Formula (2), or a salt thereof in the presence of a catalyst and a solvent. The manufacturing method 2 includes a reaction step for obtaining the benzoguanamine compound represented by the following Formula (1) having an aminomethyl group, or a salt thereof by reacting the below-described aminomethylbenzonitrile compound represented by the following Formula (3), or a salt thereof with a dicyandiamide compound represented by the following Formula (4), or a salt thereof.

[Manufacturing Method 1]
[Reduction Step]

The reduction step is a step for obtaining the benzoguanamine compound represented by the following Formula (1) having an aminomethyl group, or a salt thereof by hydrogen reduction of a cyanobenzoguanamine compound represented by the following Formula (2), or a salt thereof in the presence of a catalyst and a solvent. The hydrogen reduction reaction of a cyanobenzoguanamine compound or a salt thereof is as follows. The hydrogen reduction method may be performed, for example, by charging a reactor with a raw material (a cyanobenzoguanamine compound or a salt thereof), a catalyst, a solvent, and hydrogen for the reaction, though not particularly limited.

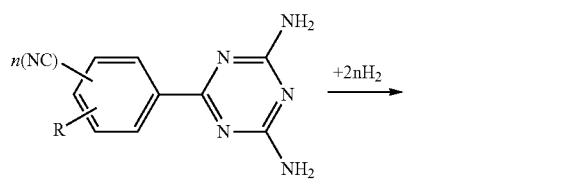

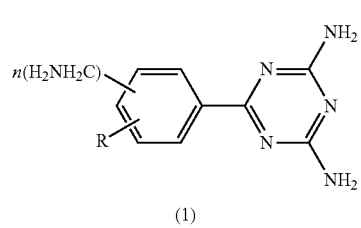

(In the Formula (1) and the Formula (2), R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.)

(Cyanobenzoguanamine Compound or Salt Thereof)

The cyanobenzoguanamine compound or a salt thereof as a raw material represented by the Formula (2) can be suitably obtained, for example, by a reaction of phthalonitrile with dicyandiamide.

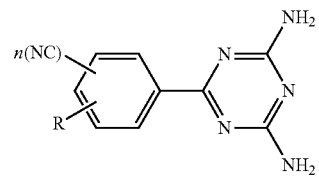

(In the Formula (2), R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.)

In the Formulas (1) and (2), examples of the alkyl group having 1 to 10 carbon atoms represented by R include a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group.

In the Formulas (1) and (2), examples of the alkoxy group having 1 to 10 carbon atoms represented by R include a methoxy group, an ethoxy group, a linear or branched propoxy group, a linear or branched butoxy group, and a cyclic cyclohexyloxy group.

In the Formulas (1) and (2), examples of the aryl group having 6 to 10 carbon atoms represented by R include a phenyl group and a benzyl group, though not particularly limited.

In the Formulas (1) and (2), examples of the aryloxy group having 6 to 10 carbon atoms represented by R include a phenoxy group, though not particularly limited.

In the Formulas (1) and (2), examples of the halogen atom represented by R include a chlorine atom, a fluorine atom and a bromine atom.

Examples of the cyanobenzoguanamine compound represented by the Formula (2), or a salt thereof include o-cyanobenzoguanamine, m-cyanobenzoguanamine, p-cyanobenzoguanamine, 3,5-dicyano-1-benzoguanamine, 3,4-dicyano-1-benzoguanamine, 2,5-dimethyl-4-cyanobenzoguanamine, and a salt thereof, though not particularly limited.

Examples of the salt of a cyanobenzoguanamine compound represented by the Formula (2) include the salt of a cyanobenzoguanamine compound with an inorganic and/or organic acid, though not particularly limited. In particular, a salt of a cyanobenzoguanamine compound with any one of hydrochloric acid, carbonic acid, and acetic acid is preferred.

(Catalyst)

The catalyst used for hydrogen reduction is not particularly limited as long as having hydrogen reduction activity, and examples thereof include a catalyst of nickel, cobalt, palladium, and a precious metal such as platinum supported in a highly dispersed state on a carrier such as silica, alumina, zirconia, titania, and magnesia; and a sponge metal catalyst made of an alloy of nickel or cobalt and aluminum treated with alkali. In particular, a nickel sponge metal catalyst is preferred, since it has high activity at a relatively low cost. The catalysts may be used alone or in combination of two or more.

The catalyst in a powder or granule form may be used in a suspended-bed reactor. Alternatively the catalyst in a pellet or crushed form may be used in a fixed-bed reactor.

The amount of the catalyst used is preferably 0.00010 to 1000 parts by mass, more preferably 0.0010 to 10 parts by mass, furthermore preferably 0.010 to 1.0 part by mass, based on 1 part by mass of a cyanobenzoguanamine compound or a salt thereof, though not particularly limited. With an amount of the catalyst used of 0.00010 parts by mass or more, the reaction tends to proceed more efficiently. With an amount of the catalyst used of 1000 parts by mass or less, more economical advantages tend to be obtained.

(Solvent)

Examples of the solvent for use in hydrogen reduction include: water; alcohols such as methanol, ethanol and propanol; hydrocarbons such as hexane, benzene, toluene, and xylene; ethers such as tetrahydrofuran; amides such as dimethylformamide; ammonia; amines such as benzylamine and xylenediamine, though not particularly limited. In particular, methyl cellosolve (2-methoxyethanol) is preferred, in which the raw materials and the products have high solubility. The solvents may be used alone or in combination of two or more.

The amount of the solvent used is preferably 0.10 to 1000 parts by mass, more preferably 1.0 to 100 parts by mass, furthermore preferably 5.0 to 50 parts by mass, based on 1 part by mass of a cyanobenzoguanamine compound or a salt thereof, though not particularly limited. With an amount of the solvent used of 0.10 parts by mass or more, the raw materials and the products tend to be more easily dissolved and the reaction tends to proceed more efficiently. With an amount of the solvent used of 1000 parts by mass or less, more economical advantages tend to be obtained.

In order to improve selectivity, a basic compound such as an alkali metal compound, an alkaline earth metal compound, and an amine compound may be added to the solvent. In particular, potassium hydroxide and sodium hydroxide are preferred from the viewpoints of the effect of addition and the economy. The basic compounds may be used alone or in combination of two or more.

(Hydrogen)

A large excess amount of hydrogen is typically used based on a cyanobenzoguanamine compound or a salt thereof for hydrogen reduction, though not particularly limited. The hydrogen for use may be diluted with nitrogen or a rare gas which is stable in the reaction conditions.

The reaction method may be arbitrarily chosen from a batch type and a continuous flow type. In the batch type, the sequence of addition of raw materials may be also arbitrarily selected.

A benzoguanamine compound having an aminomethyl group, or a salt thereof may be easily collected from the reaction liquid by a conventional method such as distillation, recrystallization, and extraction.

The reaction pressure is preferably 0 to 100 MPa, more preferably 1 to 10 MPa, furthermore preferably 2 to 6 MPa, though not particularly limited.

The reaction temperature may be appropriately adjusted depending on the charging ratio of raw materials and reaction conditions, being preferably 20 to 200° C., more preferably 40 to 150° C., furthermore preferably 50 to 100° C.

The reaction time may be appropriately adjusted depending on the charging ratio of raw materials and reaction conditions, being preferably 1 to 1000 minutes, more preferably 5 to 500 minutes, furthermore preferably 10 to 300 minutes, in a batch method.

[Manufacturing Method 2]
[Reaction Process]

The reaction step includes reacting an aminomethylbenzonitrile compound represented by the following Formula (3), or a salt thereof with a dicyandiamide compound represented by the following Formula (4), or a salt thereof so as to obtain a benzoguanamine compound having an aminomethyl group represented by the following Formula (1). The reaction of an aminomethylbenzonitrile compound or a salt thereof with a dicyandiamide compound or a salt thereof is represented by the following formula.

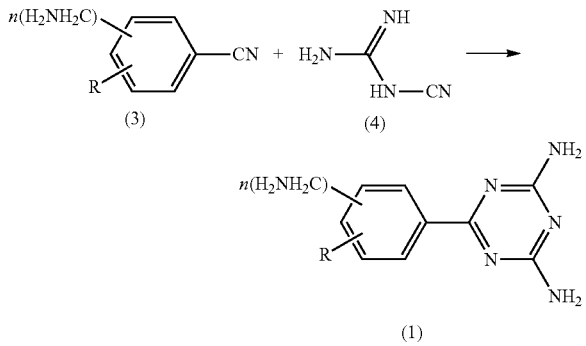

(In the Formula (3), R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom, and n is an integer of 1 to 2.)

(Aminomethylbenzonitrile Compound and Salt Thereof)

In the Formula (3), examples of the alkyl group having 1 to 10 carbon atoms represented by R include a methyl group, an ethyl group, a linear or branched propyl group, a linear or branched butyl group, a linear or branched pentyl group, a linear or branched hexyl group, a linear or branched heptyl group, a linear or branched octyl group, a linear or branched nonyl group, a linear or branched decyl group, and a cyclic cyclohexyl group.

In the Formula (3), examples of the alkoxy group having 1 to 10 carbon atoms represented by R include a methoxy group, an ethoxy group, a linear or branched propoxy group, a linear or branched butoxy group, and a cyclic cyclohexyloxy group.

In the Formula (3), examples of the aryl group having 6 to 10 carbon atoms represented by R include a phenyl group and a benzyl group, though not particularly limited.

In the Formula (3), examples of the aryloxy group having 6 to 10 carbon atoms represented by R include a phenoxy group, though not particularly limited.

In the Formula (3), examples of the halogen atom represented by R include a chlorine atom, a fluorine atom and a bromine atom. A salt obtained by neutralizing an amino group of an aminomethylbenzonitrile compound or a salt thereof with an acid such as hydrochloric acid may be also used in the reaction process.

Examples of the aminomethylbenzonitrile compound or a salt thereof, represented by the Formula (3) include o-aminomethylbenzonitrile, m-aminomethylbenzonitrile, p-aminomethylbenzonitrile, 3,5-bis(aminomethyl)benzonitrile, 2,5-bis(aminomethyl)benzonitrile, 2,4-bis(aminomethyl) benzonitrile, and a salt thereof, though not particularly limited.

Examples of the salt of an aminomethylbenzonitrile compound represented by the Formula (3) include a salt of an aminomethylbenzonitrile compound with an inorganic and/or organic acid, though not particularly limited. In particular, a salt of an aminomethylbenzonitrile compound with any one of hydrochloric acid, carbonic acid, and acetic acid is preferred.

(Catalyst)

In the reaction between an aminomethylbenzonitrile compound or a salt thereof and a dicyandiamide compound or a salt thereof, a catalyst may be used. Preferred examples of the catalyst for use include a basic compound such as an alkali metal compound and an alkali earth metal compound, though not particularly limited.

Examples of the alkali metal compound and the alkali earth metal compound include a hydroxide, fluoride, a chloride, a bromide, a iodide, an oxide, a sulfide, a carbonate, a hydrogen carbonate, a sulfate, and an organic acid salt of lithium, sodium, potassium, rubidium, beryllium, magnesium, calcium, strontium, or barium though not particularly limited. In particular, potassium hydroxide is preferred, due to easy availability at low cost.

The amount of the catalyst used is preferably 0.00010 to 100 mol, more preferably 0.0010 to 10 mol, furthermore preferably 0.0050 to 5.0 mol, based on 1 mol of an aminomethylbenzonitrile compound or a salt thereof, though not particularly limited. With an amount of the catalyst used of 0.00010 mol or more, the reaction tends to proceed more efficiently. With an amount of the catalyst used of 100 mol or less, more economical advantages tend to be obtained. In particular, when an aminomethylbenzonitrile salt is used, the amount of the catalyst used is preferably an equivalent or more based on 1 mol of the aminomethylbenzonitrile salt.

(Solvent)

In the reaction between an aminomethylbenzonitrile compound or a salt thereof and a dicyandiamide compound or a salt thereof, a solvent may be used. Examples of the solvent for use include: water; alcohols such as methanol, ethanol, propanol, and butanol; hydrocarbons such as hexane, benzene, toluene, and xylene; ethers such as tetrahydrofuran; amides such as dimethylformamide; amines such as benzylamine and xylenediamine, though not particularly limited. The solvents may be used alone or in combination of two or more. In particular, methyl cellosolve (2-methoxyethanol), butanol, and methanol are preferred, in which the raw materials and the products have high solubility.

The amount of the solvent used is preferably 0.10 to 1000 parts by mass, more preferably 1.0 to 100 parts by mass, furthermore preferably 5.0 to 50 parts by mass, based on 1 part by mass of a cyanobenzoguanamine compound or a salt thereof as raw material, though not particularly limited. With an amount of the solvent used of 0.10 parts by mass or more, the reaction tends to proceed more efficiently. With an amount of the solvent used of 1000 parts by mass or less, more economical advantages tend to be obtained.

Examples of the atmosphere for the reaction include nitrogen or a rare gas which is stable in the reaction system, though not particularly limited.

The reaction method may be arbitrarily chosen from a batch type and a continuous flow type. In the batch type, the sequence of addition of raw materials may be also arbitrarily selected.

A benzoguanamine compound having an aminomethyl group, or a salt thereof may be easily collected from the reaction liquid by a conventional method such as distillation, recrystallization, and extraction. A method for collecting crystals from the reaction liquid by using a solvent in which an aminomethylbenzonitrile compound or a salt thereof as raw material is easily dissolved and a benzoguanamine compound having an aminomethyl group, or a salt thereof as product is hardly dissolved, is particularly simple and preferable.

The preferred reaction pressure may be a pressure under normal-pressure reflux conditions or under self-pressure conditions of the solvent in a closed vessel, though not particularly limited.

The reaction temperature may be appropriately adjusted depending on the charging ratio of raw materials and reaction conditions, being preferably 20 to 300° C., more preferably 50 to 250° C., furthermore preferably 70 to 200° C.

The reaction time may be appropriately adjusted depending on the charging ratio of raw materials and reaction conditions, being preferably 1 minute to 100 hours, more preferably 5 minutes to 50 hours, furthermore preferably 10 minutes to 10 hours, in a batch method.

The benzoguanamine compound having an aminomethyl group, or a salt thereof in the present embodiment may be used as raw material for thermosetting resins having excellent properties in terms of compatibility with an oil-soluble resin, water resistance, chemical resistance, heat resistance, surface gloss, electrical properties, stain resistance, and crack resistance.

EXAMPLES

Hereinafter, the present invention is more specifically described with reference to Examples and Comparative Examples. The present invention is not limited by the following Examples in any manner.

Commercially available reagents (manufactured by Wako Pure Chemical Industries, Ltd., Tokyo Chemical Industry Co., Ltd., or Sigma-Aldrich Co. LLC.) were used as raw materials. Each component was identified by NMR (deuterated DMSO solvent), IR, or GC-MS spectroscopy. Furthermore, analysis of the reaction liquid was performed by gas chromatography with an internal standard. The yield is represented in mol %.

Synthesis Example 1

Synthesis of m-cyanobenzoguanamine

A 200 mL three-neck flask equipped with a thermometer sheath tube and a reflux condenser was charged with 12.8 g of isophthalonitrile, 8.45 g of dicyandiamide, 0.95 g of potassium hydroxide, and 128 g of 1-butanol. The mixture was heated to reflux at 120° C. for 1 hour under agitation at normal pressure. Subsequently, crystals precipitated after cooling were filtered off and washed with a small amount of methanol, and then vacuum-dried to obtain m-cyanobenzoguanamine at a yield of 81%.

Synthesis Example 2

Synthesis of p-cyanobenzoguanamine

Except that terephthalonitrile was used instead of isophthalonitrile, the same procedures were repeated as in Synthesis Example 1, so that p-cyanobenzoguanamine was obtained at a yield of 85%.

Synthesis Example 3

Synthesis of 2,5-dimethyl-4-cyanobenzoguanamine

A 200 mL three-neck flask equipped with a thermometer sheath tube and a reflux condenser was charged with 3.8 g of 2,5-dimethylterephthalonitrile, 2.2 g of dicyandiamide, 0.21 g of potassium hydroxide, and 52 g of 1-butanol. The mixture was heated to reflux at 120° C. for 1 hour under agitation at normal pressure. Subsequently, crystals precipitated after cooling were filtered off and washed with a small amount of methanol, and then vacuum-dried to obtain 2,5-dimethyl-4-cyanobenzoguanamine at a yield of 98%.

Example 1

Figure 2:
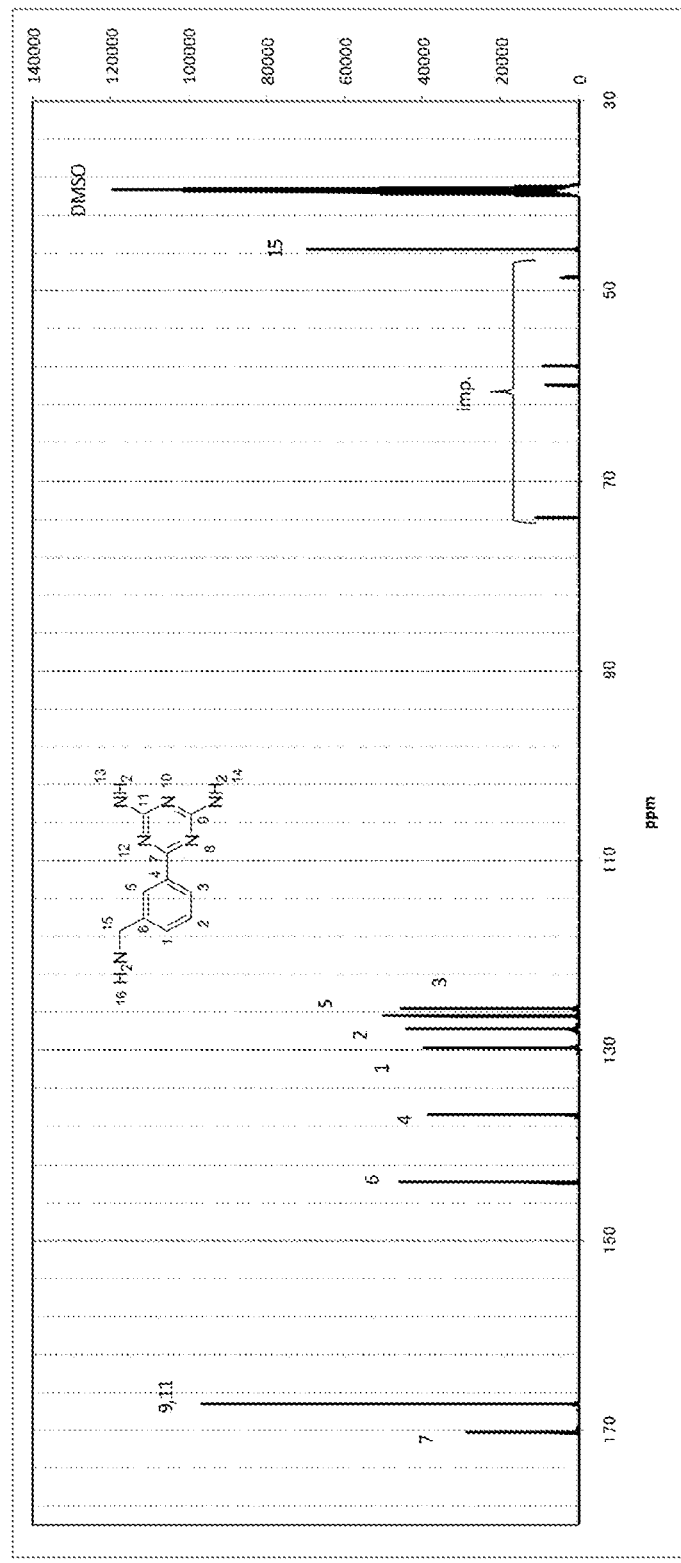
FIG. 2 shows a $^{13}$C-NMR chart of m-aminomethylbenzoguanamine.
Figure 3:
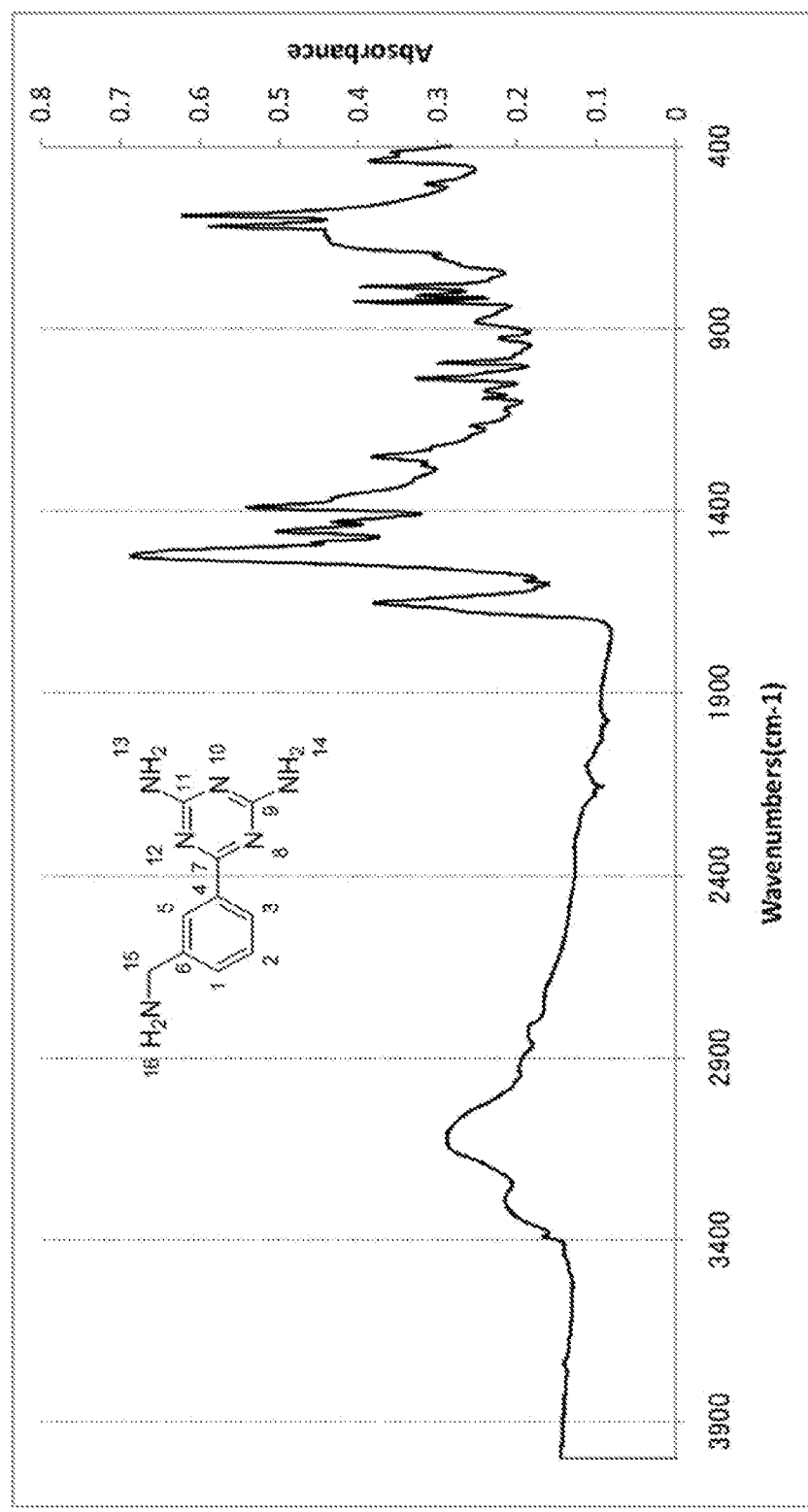
FIG. 3 shows an IR chart of m-aminomethylbenzoguanamine.
Figure 4:
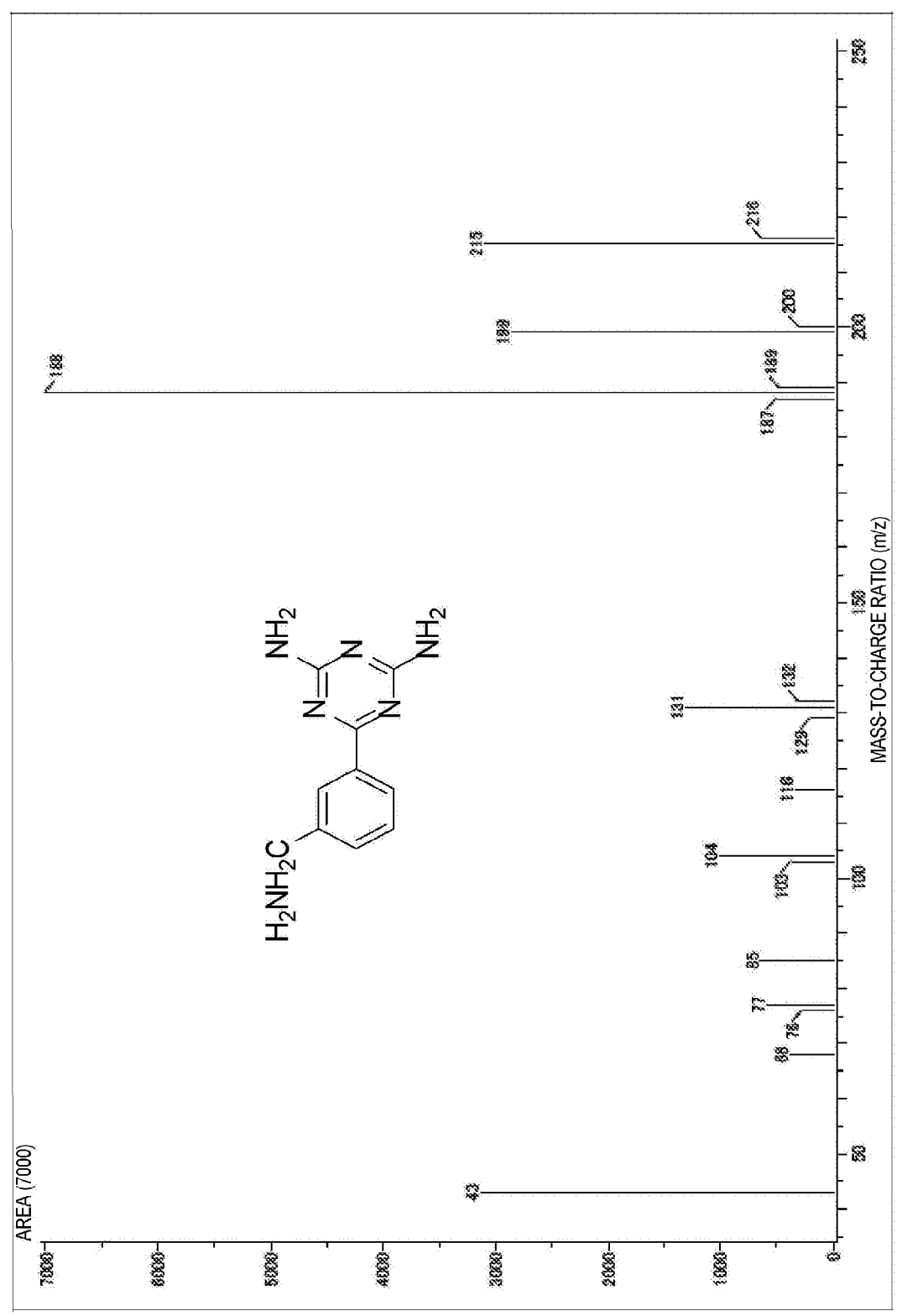
FIG. 4 shows a GC-MS EI+ chart of m-aminomethylbenzoguanamine.
Figure 5:
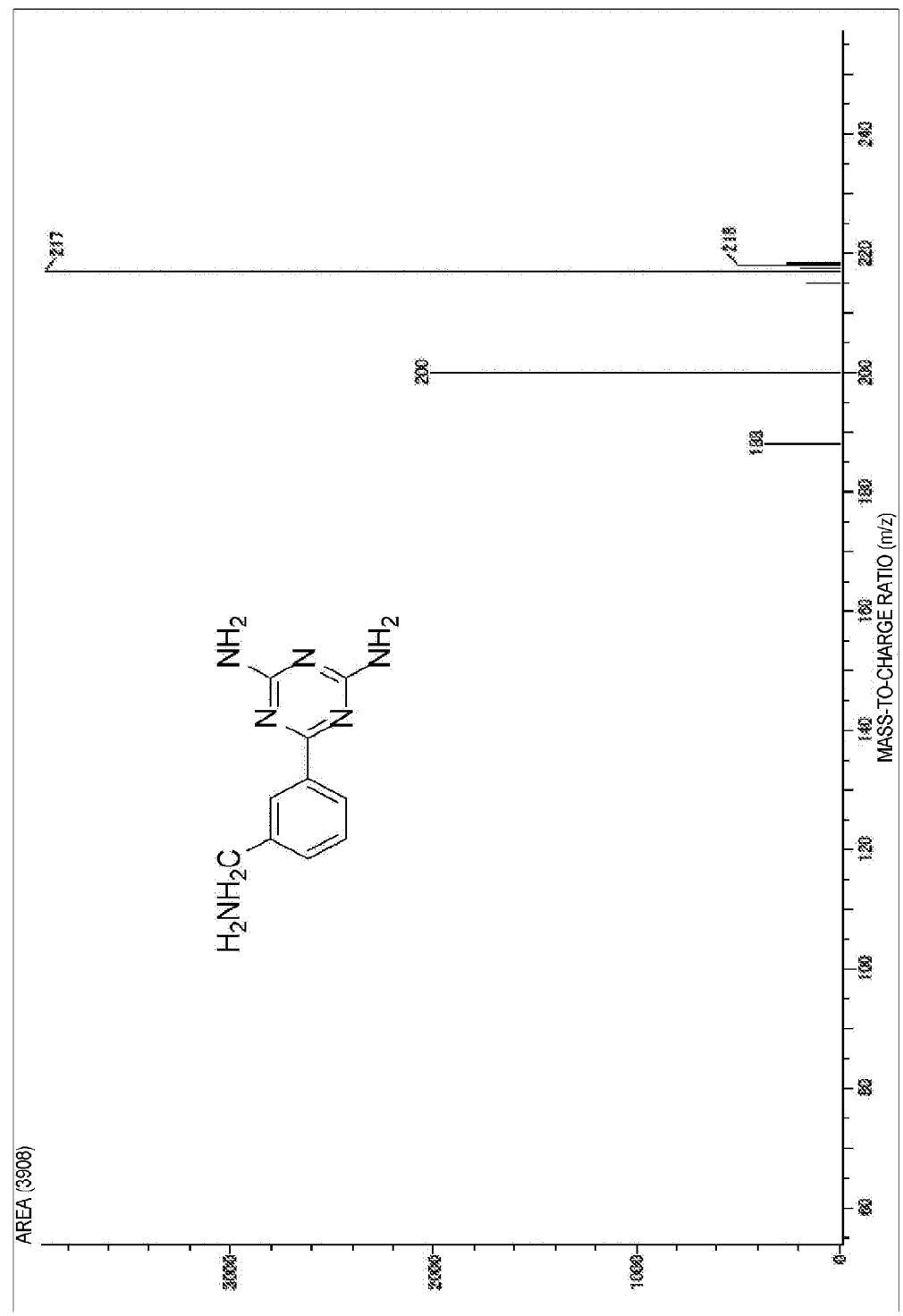
FIG. 5 shows a GC-MS CI+ chart of m-aminomethylbenzoguanamine.

A pressure resistant vessel of stainless steel with an inner volume of 100 mL equipped with a thermometer sheath tube and a pressure gauge was charged with 3.2 g of m-cyanobenzoguanamine obtained in Synthesis Example 1, 0.14 g of sodium hydroxide, 0.5 g of a commercially available sponge nickel catalyst (R-200 manufactured by Nikko Rica Corporation), and 30 g of methyl cellosolve as solvent. After the atmosphere in the reaction vessel was substituted with nitrogen, hydrogen at 5 MPa was applied to the interior to be sealed. The vessel was heated and held at 60° C. for 2 hours under agitation. After cooling and reduction in pressure, the catalyst and insoluble substances were separated from the reaction liquid. The solvent was further condensed with an evaporator, and the product was recrystallized with methyl cellosolve, so that white crystals were obtained as a main product. It was confirmed that the white crystal was m-aminomethylbenzoguanamine by $^1$H and $^{13}$C-NMR charts (FIGS. 1 and 2), an IR chart (FIG. 3), and EI+ and CI+ mass spectra of GC-MS (FIGS. 4 and 5). As a result of gas chromatography analysis of the solution obtained by separating the catalyst and insoluble substances from the reaction liquid, the yield of m-aminomethylbenzoguanamine was 90%.

Example 2

Figure 6:
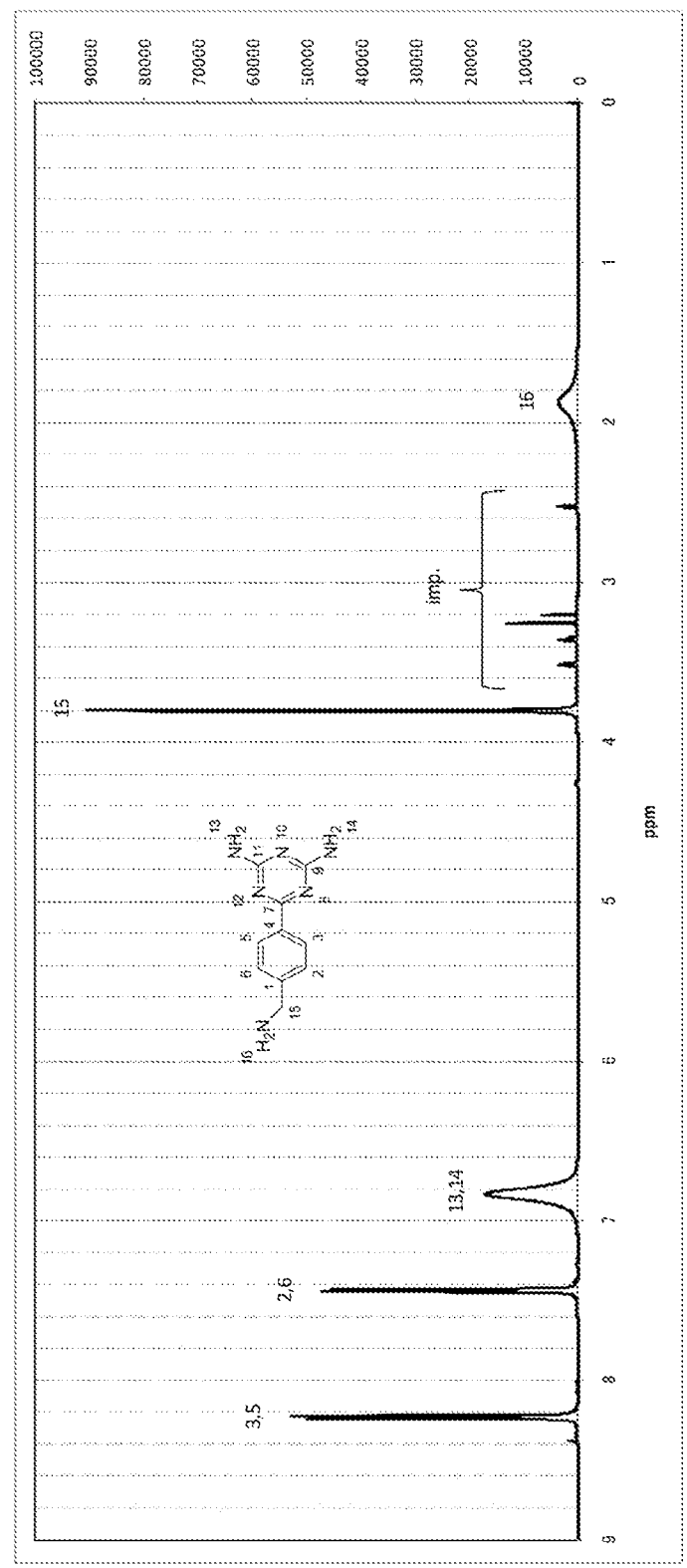
FIG. 6 shows a $^1$H-NMR chart of p-aminomethylbenzoguanamine.
Figure 7:
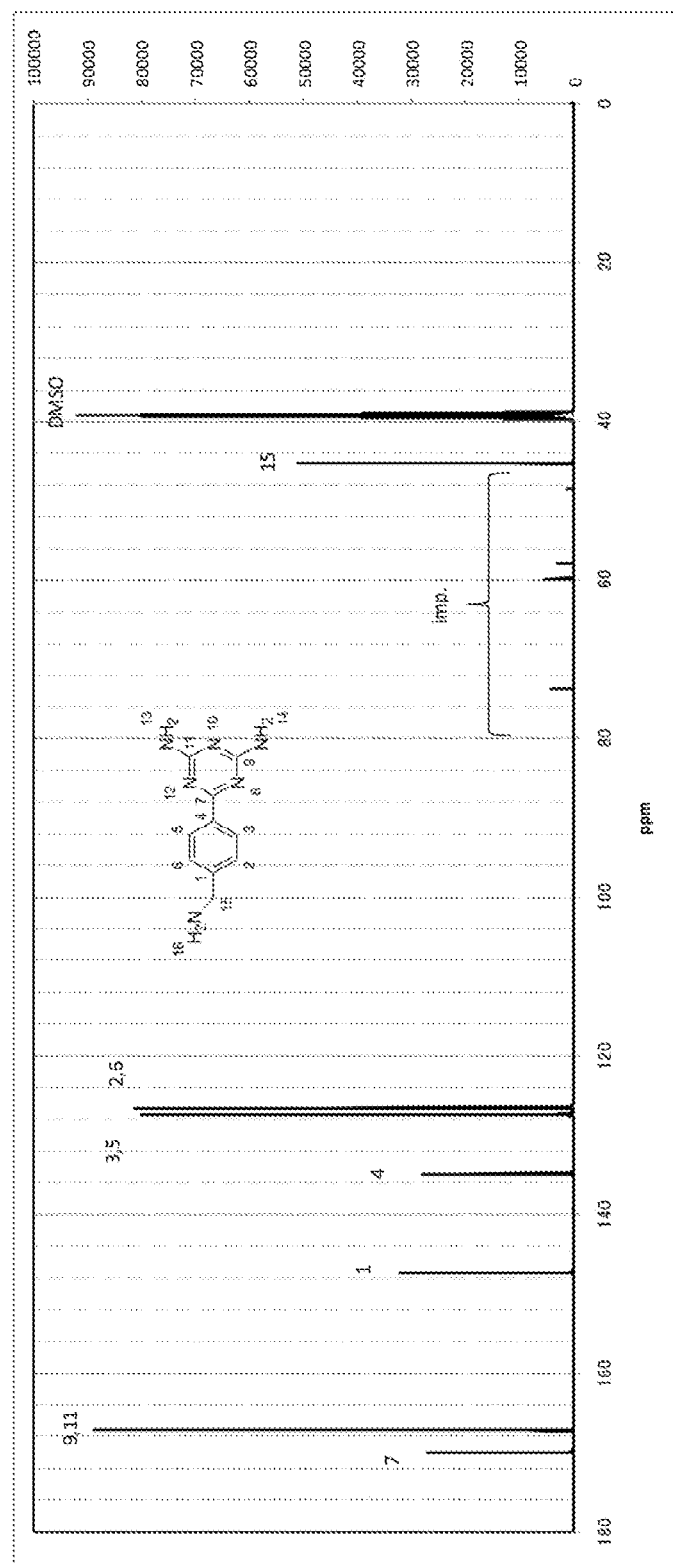
FIG. 7 shows a $^{13}$C-NMR chart of p-aminomethylbenzoguanamine.
Figure 8:
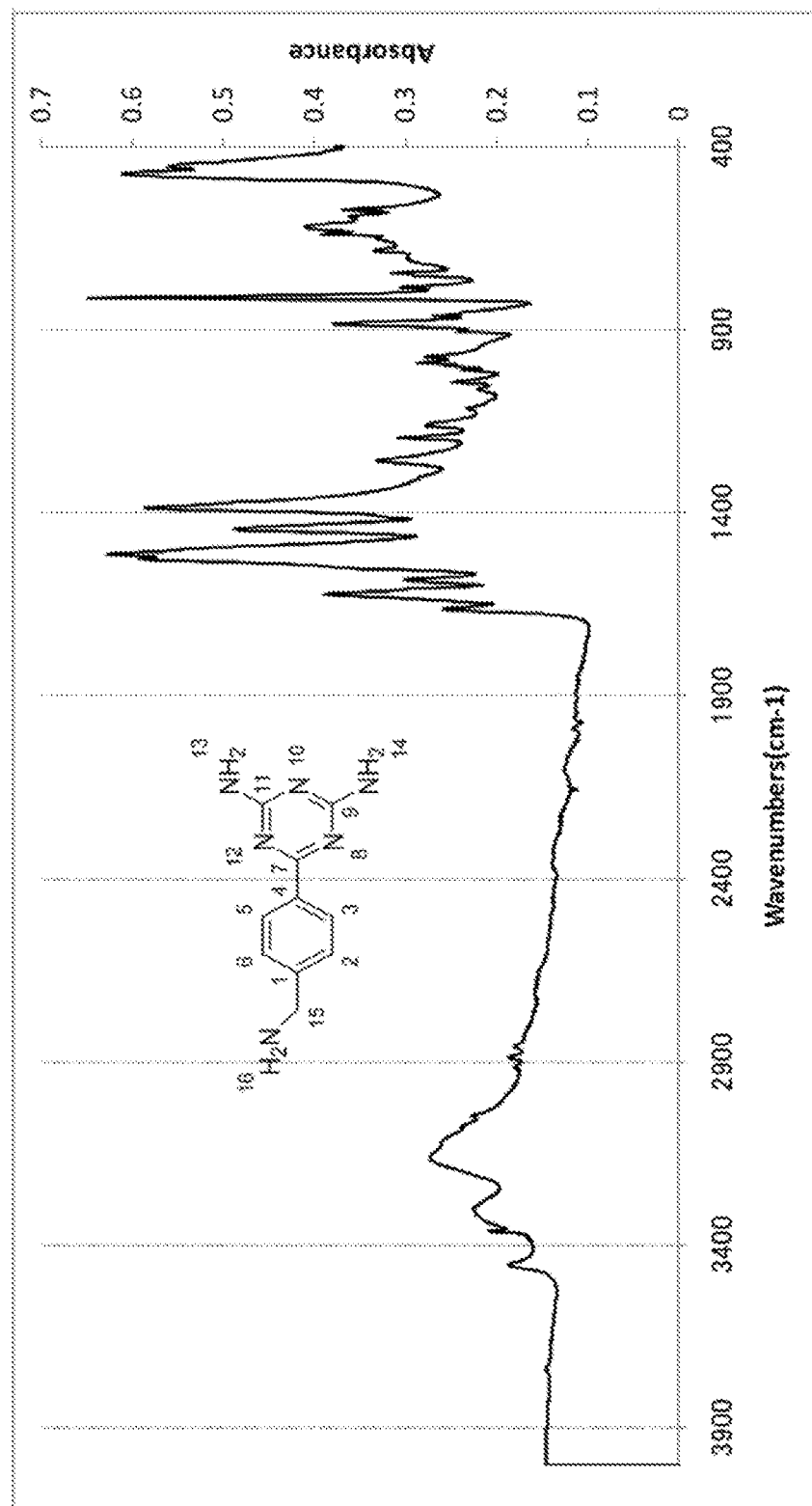
FIG. 8 shows an IR chart of p-aminomethylbenzoguanamine.
Figure 9:
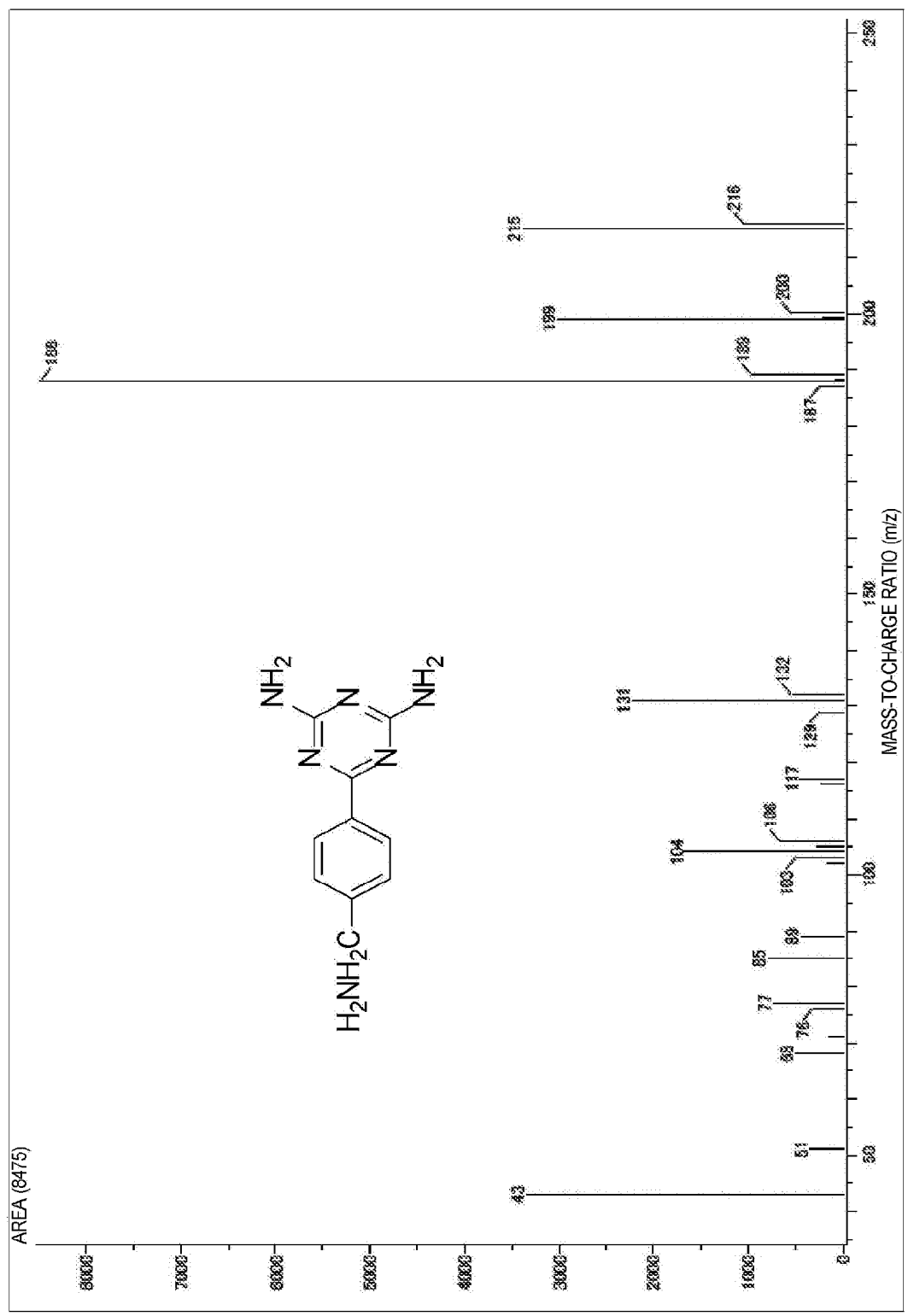
FIG. 9 shows a GC-MS EI+ chart of p-aminomethylbenzoguanamine.
Figure 10:
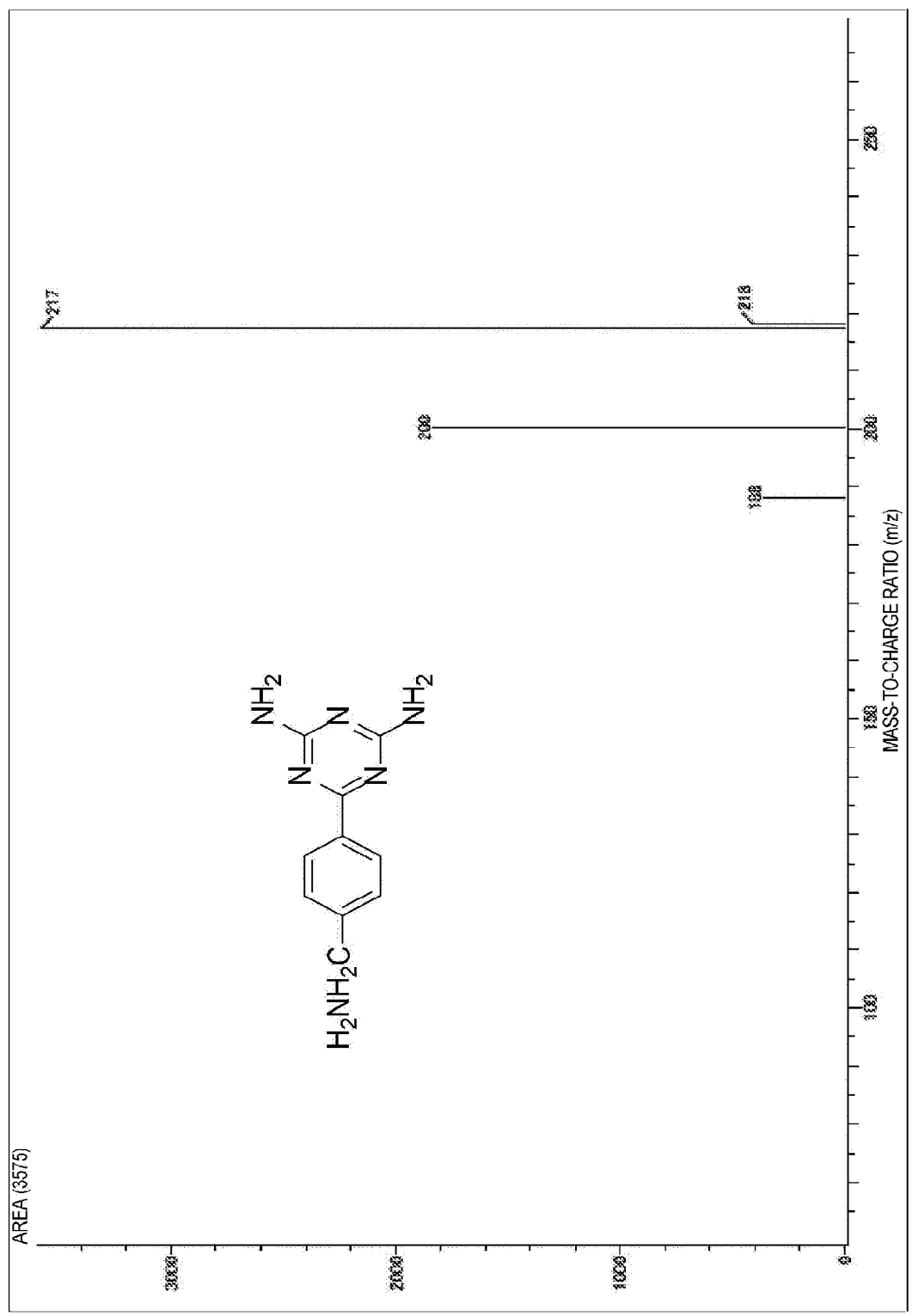
FIG. 10 shows a GC-MS CI+ chart of p-aminomethylbenzoguanamine.

The same reaction vessel as in Example 1 was charged with 1.5 g of p-cyanobenzoguanamine obtained in Synthesis Example 2, 0.08 g of sodium hydroxide, 0.5 g of a commercially available sponge nickel catalyst (R-200 manufactured by Nikko Rica Corporation), and 30 g of methyl cellosolve as solvent. After the atmosphere in the reaction vessel was substituted with nitrogen, hydrogen at 5 MPa was applied to the interior to be sealed. The vessel was heated and held at 60° C. for 1 hour under agitation. After cooling and reduction in pressure, the catalyst and insoluble substances were separated from the reaction liquid. The solvent was further condensed with an evaporator, and the product was recrystallized with methyl cellosolve, so that white crystals were obtained as main product. It was confirmed that the white crystal was p-aminomethylbenzoguanamine by $^1$H and $^{13}$C-NMR charts (FIGS. 6 and 7), an IR chart (FIG. 8), and EI+ and CI+ mass spectra of GC-MS (FIGS. 9 and 10). As a result of gas chromatography analysis of the solution obtained by separating the catalyst and insoluble substances from the reaction liquid, the yield of p-aminomethylbenzoguanamine was 91%.

Example 3

A pressure resistant vessel of stainless steel with an inner volume of 300 mL equipped with a thermometer sheath tube and a pressure gauge was charged with 9.0 g of p-cyanobenzoguanamine obtained in Synthesis Example 2, 0.45 g of sodium hydroxide, 1.5 g of a commercially available sponge nickel catalyst (R-200 manufactured by Nikko Rica Corporation), and 90 g of methyl cellosolve as solvent. After the atmosphere in the reaction vessel was substituted with nitrogen, hydrogen at 5 MPa was applied to the interior to be sealed. The vessel was heated and held at 80° C. for 2 hours under agitation. After cooling and reduction in pressure, the catalyst and insoluble substances were separated from the reaction liquid. As a result of gas chromatography analysis of the solution, the yield of p-aminomethylbenzoguanamine was 85%. The solvent was further condensed with an evaporator, and the product was recrystallized with methyl cellosolve, so that 7.1 g of white crystals were obtained as main product. As a result of gas chromatography analysis of the white crystals, the purity of p-aminomethylbenzoguanamine was 95% and the yield of the crystal p-aminomethylbenzoguanamine relative to the prepared P-cyanobenzoguanamine was 73%.

Example 4

Figure 11:
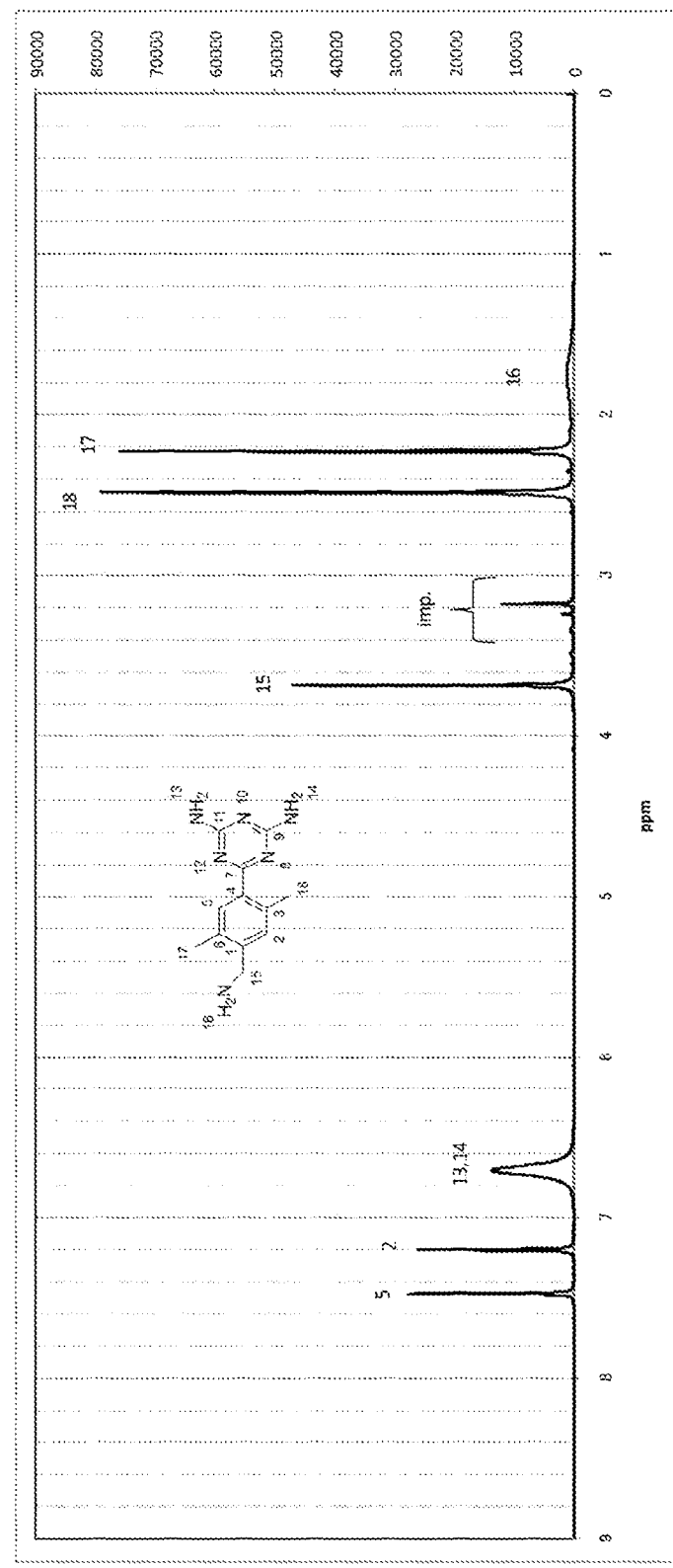
FIG. 11 shows a $^1$H-NMR chart of 2,5-dimethyl-4-aminomethylbenzoguanamine.
Figure 12:
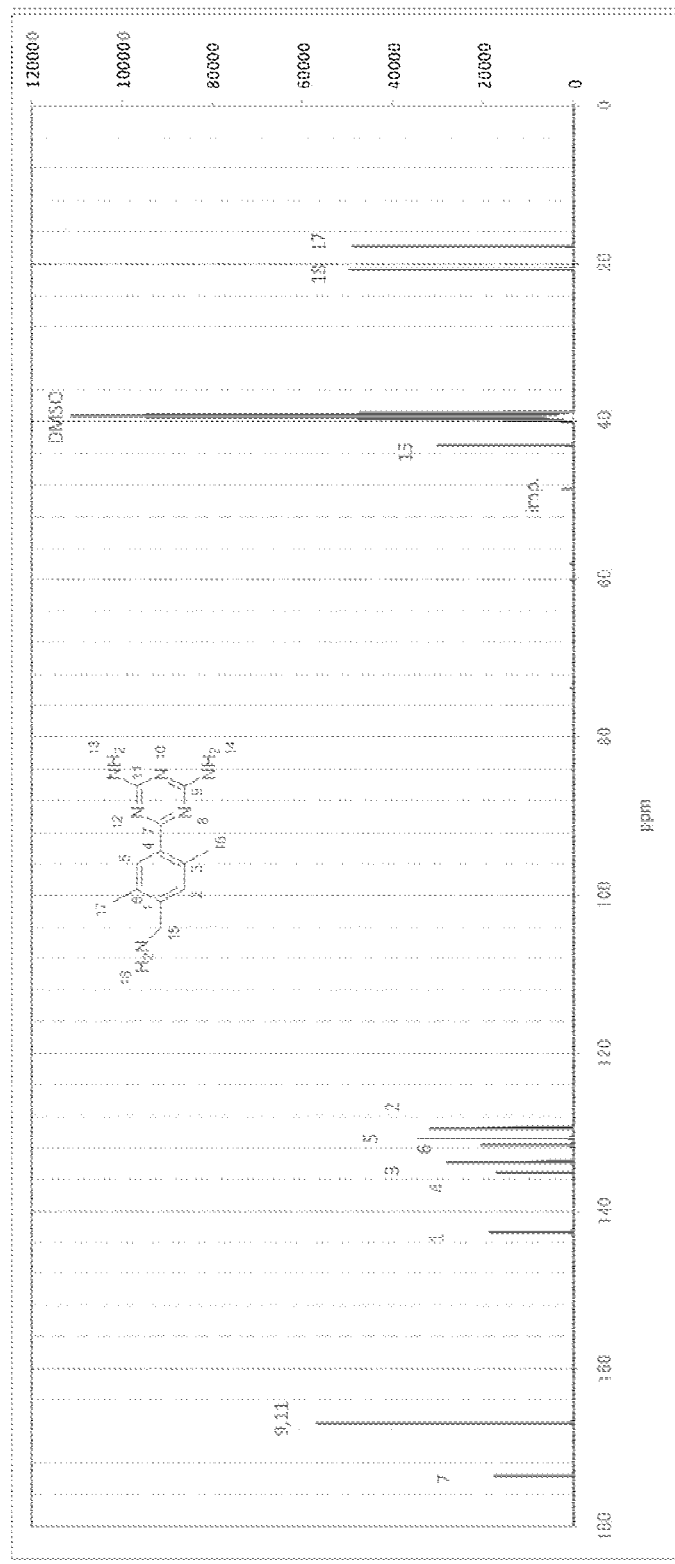
FIG. 12 shows a $^{13}$C-NMR chart of 2,5-dimethyl-4-aminomethylbenzoguanamine.
Figure 13:
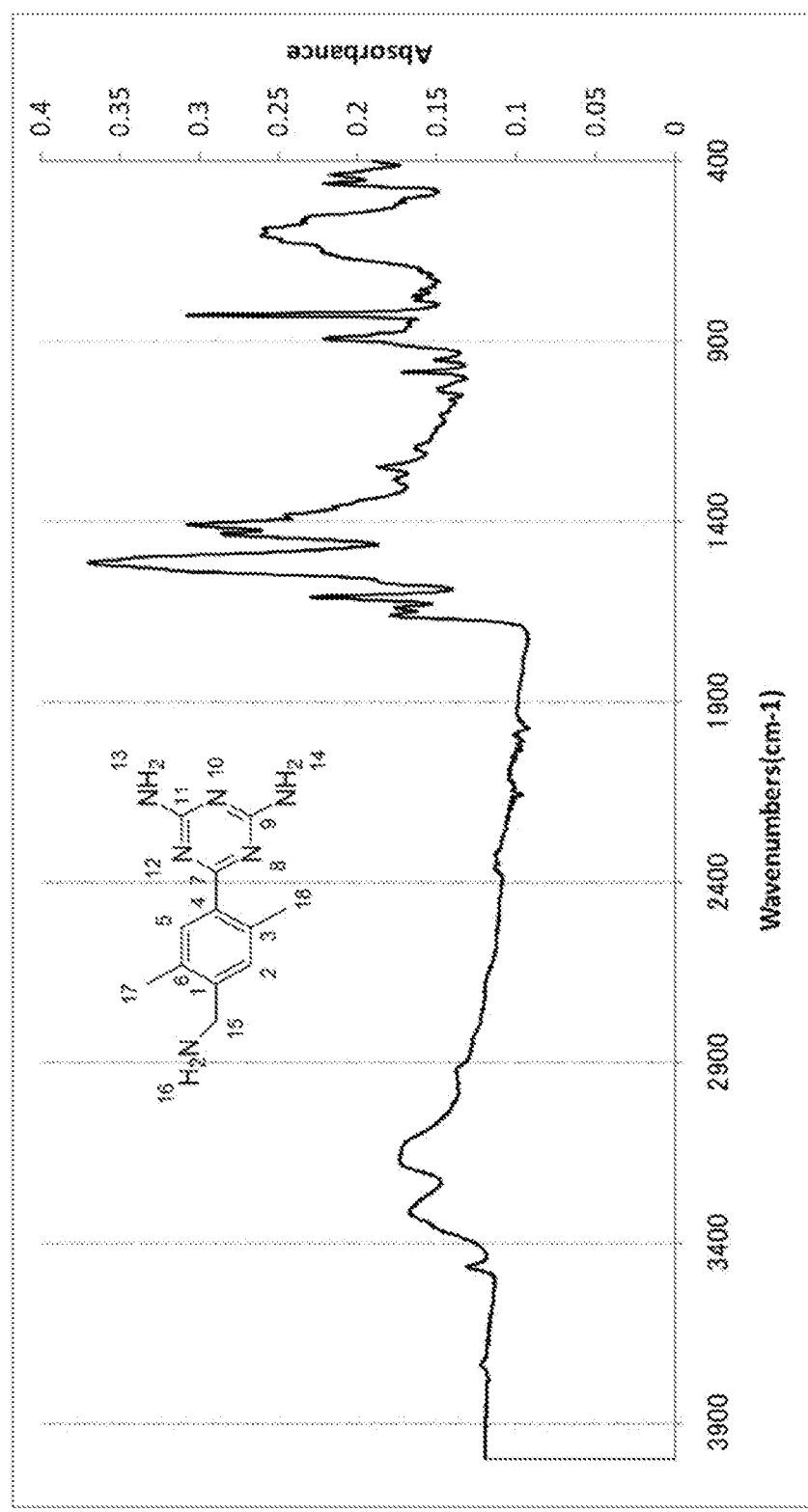
FIG. 13 shows an IR chart of 2,5-dimethyl-4-aminomethylbenzoguanamine.
Figure 14:
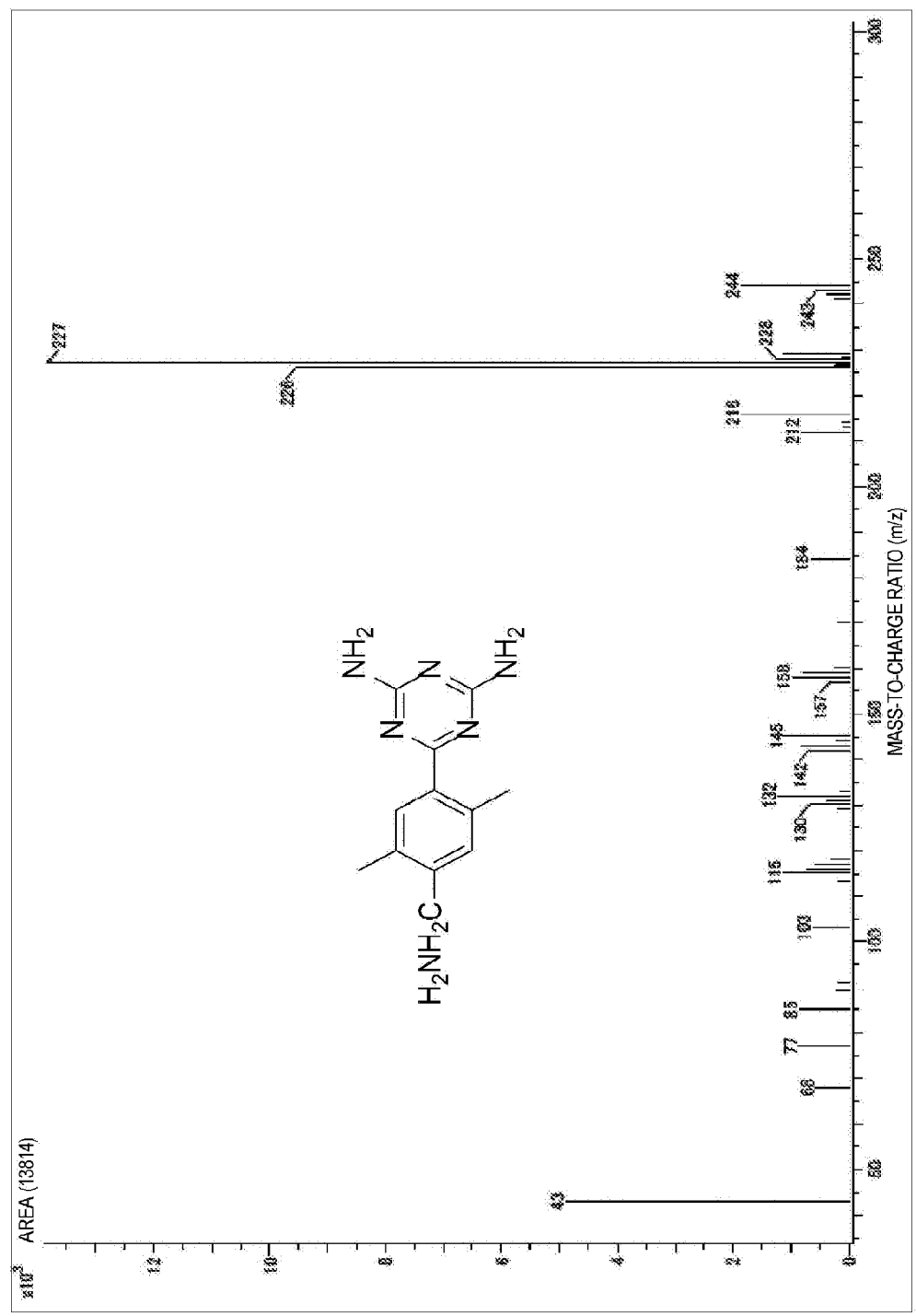
FIG. 14 shows a GC-MS EI+ chart of 2,5-dimethyl-4-aminomethylbenzoguanamine.
Figure 15:
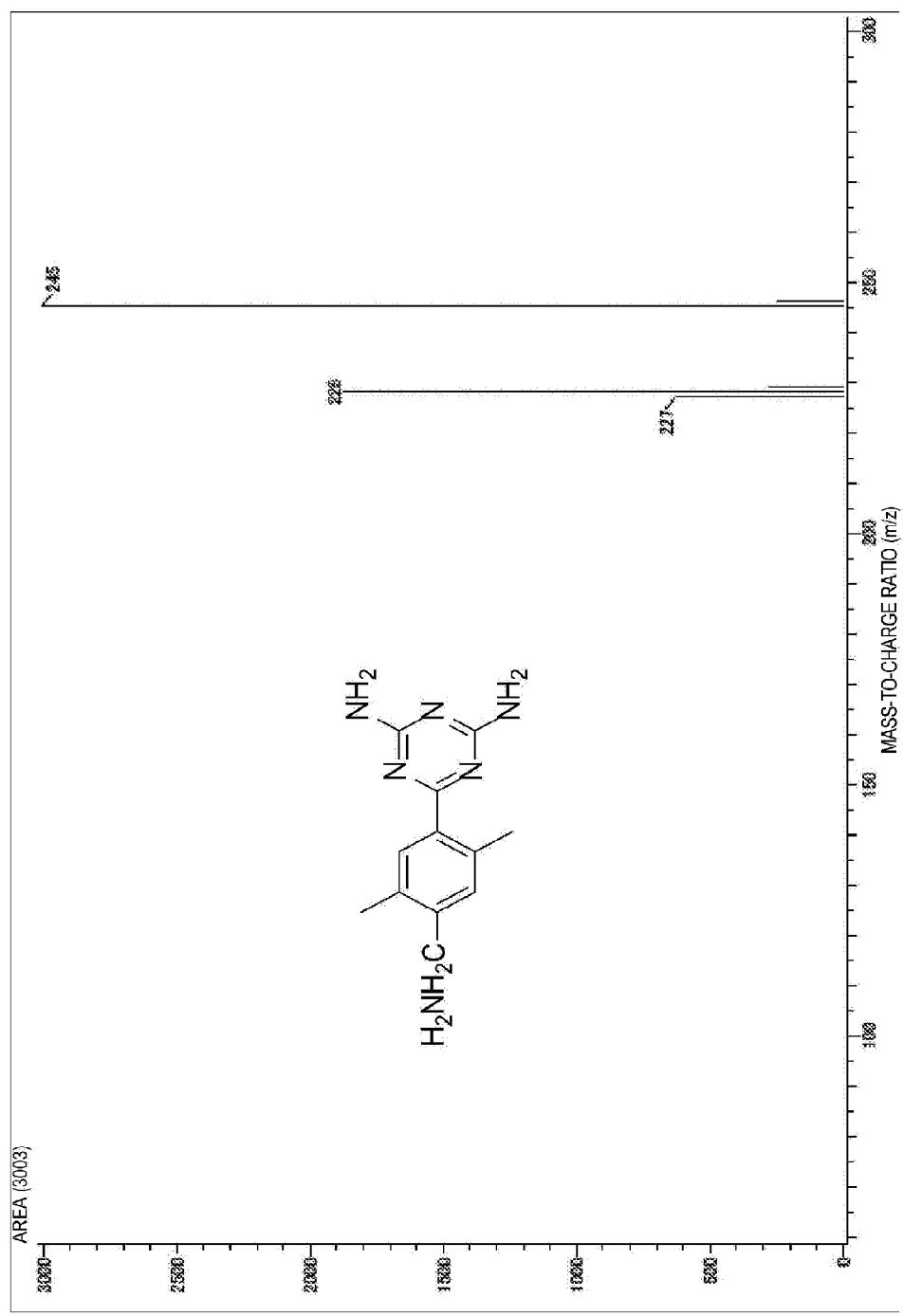
FIG. 15 shows a GC-MS CI+ chart of 2,5-dimethyl-4-aminomethylbenzoguanamine.

The same reaction vessel as in Example 1 was charged with 1.8 g of 2,5-dimethyl-4-cyanobenzoguanamine obtained in Synthesis Example 3, 0.14 g of sodium hydroxide, 0.5 g of a commercially available sponge nickel catalyst (R-200 manufactured by Nikko Rica Corporation), and 30 g of methyl cellosolve as solvent. After the atmosphere in the reaction vessel was substituted with nitrogen, hydrogen at 5 MPa was applied to the interior to be sealed. The vessel was heated and held at 100° C. for 3 hours under agitation. After cooling and reduction in pressure, the catalyst and insoluble substances were separated from the reaction liquid. The solvent was further condensed with an evaporator, and the product was recrystallized with methyl cellosolve, so that white crystals were obtained. It was confirmed that the white crystal was 2,5-dimethyl-4-aminomethylbenzoguanamine by $^1$H and $^{13}$C-NMR charts (FIGS. 11 and 12), an IR chart (FIG. 13), and EI+ and CI+ mass spectra of GC-MS (FIGS. 14 and 15). As a result of gas chromatography analysis of the solution obtained by separating the catalyst and insoluble substances from the reaction liquid, the yield of 2,5-dimethyl-4-aminomethylbenzoguanamine was 90%.

Example 5

Except that a sponge cobalt catalyst (R2724 manufactured by W. R. Grace & Co.) was used instead of the sponge nickel catalyst, the reaction vessel was charged with the same raw materials as in Example 1. After the atmosphere in the reaction vessel was substituted with nitrogen, hydrogen at 5 MPa was applied to the interior of the vessel to be sealed. The vessel was heated and held at 80° C. for 3 hours under agitation. After cooling and reduction in pressure, the catalyst and insoluble substances were separated from the reaction liquid. As a result of gas chromatography analysis of the solution, the yield of m-aminomethylbenzoguanamine was 86%.

Example 6

A 200 mL three-neck flask equipped with a thermometer sheath tube and a reflux condenser was charged with 2.0 g of 3-cyanobenzylamine, 1.0 g of dicyandiamide, 0.1 g of potassium hydroxide, 12.0 g of m-xylenediamine and 25 g of 1-butanol. The mixture was heated to reflux at 120° C. for 5 hours under agitation at normal pressure. Subsequently, crystals precipitated after cooling were filtered off and washed with a small amount of methanol, and then vacuum-dried to obtain white crystals. It was confirmed that the white crystals were m-aminomethylbenzoguanamine based on the retention time in gas chromatography. The yield of m-aminomethylbenzoguanamine was 74%.

Example 7

A 200 mL three-neck flask equipped with a thermometer sheath tube and a reflux condenser was charged with 2.1 g of 4-aminomethylbenzonitrile hydrochloric acid salt, 1.1 g of dicyandiamide, 1.0 g of potassium hydroxide, and 25 g of 1-butanol. The mixture was heated to reflux at 120° C. for 7 hours under agitation at normal pressure. Subsequently, crystals precipitated after cooling were filtered off and washed with a small amount of methanol, and then vacuum-dried to obtain white crystals. It was confirmed that the white crystals were p-aminomethylbenzoguanamine based on the retention time in gas chromatography. The yield of p-aminomethylbenzoguanamine was 57%.

Example 8

A pressure resistant vessel of stainless steel with an inner volume of 20 mL equipped with a thermometer sheath tube and a pressure gauge was charged with 0.4 g of 4-aminomethylbenzonitrile hydrochloric acid salt, 0.2 g of dicyandiamide, 0.21 g of potassium hydroxide, and 5 g of methanol. The vessel was sealed and held at 160° C. for 2 hours under agitation. After cooling, the product was dissolved in tetrahydrofuran. As a result of gas chromatography analysis, the yield of p-aminomethylbenzoguanamine was 52%.

Example 9

To 4.5 g of an epoxy resin (JER828 manufactured by Mitsubishi Chemical Corporation), 0.87 g of m-aminomethylbenzoguanamine was added, and the mixture was agitated, mixed, and then heated at 180° C. for 2 hours, so that a transparent pale yellow cured resin was obtained. As a result of DSC analysis of the cured resin (temperature rising rate: 10° C./min, temperature measurement range: 50 to 300° C., nitrogen atmosphere), the glass transition temperature was 138° C. The results are shown in Table 1.

Examples 10 to 11

Except that the compounds shown in Table 1 were used instead of m-aminomethylbenzoguanamine, the same procedures were repeated to obtain cured resins as in Example 9. The results are shown in Table 1.

Comparative Example 1

Except that m-xylenediamine which is known as an amine-based epoxy resin curing agent as described on p. 124 in "Review of Epoxy Resins (edited by The Japan Society of Epoxy Resin Technology) vol. 1, Basics I" was used instead of m-aminomethylbenzoguanamine, the same procedures were repeated to obtain a cured resin as in Example 9. The results are shown in Table 1.

TABLE 1

| Raw material amine | Weight (g) | Color of cured resin | Glass transition temperature |
|---|---|---|---|
| Example 9 m-Aminomethylbenzoguanamine | 0.87 | Transparent pale yellow | 138° C. |
| Example 10 p-Aminomethylbenzoguanamine | 0.87 | Transparent pale yellow | 125° C. |
| Example 11 2,5-Dimethyl-4-aminomethylbenzoguanamine | 0.99 | Transparent pale yellow | 151° C. |
| Comparative Example 1 m-Xylenediamine | 0.82 | Transparent pale yellow | 111° C. |

As shown in Table 1, a cured epoxy resin excellent in heat resistance with a high glass transition temperature can be obtained by using the benzoguanamine having an aminomethyl group of the present invention as an epoxy resin curing agent, so that the present invention has great significance.

The present application is based on Japanese Patent Application filed to Japan Patent Office on Aug. 5, 2013 (Japanese Patent Application No. 2013-162021), contents of which are incorporated herein by reference.

INDUSTRIAL APPLICABILITY

A benzoguanamine compound having an aminomethyl group of the present invention, or a salt thereof can be an important compound in organic synthetic chemistry as raw material for thermosetting resins, having industrial applicability as: a thickener for epoxy curing materials, coating materials, molding resins, decorative boards, resins for processing fiber and paper, adhesives, and heat-resistant lubricant; a raw material or an additive for polyamide; an agent for preventing resist peeling; a UV ray absorber; or a raw material for medical drugs.

The invention claimed is:

1. A benzoguanamine compound having an amino methyl group, represented by the following Formula (1), or a salt thereof:

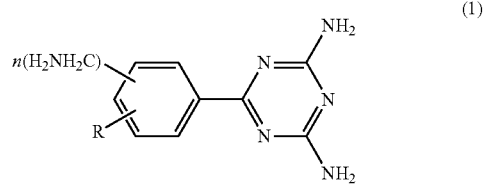

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom, and n is an integer of 1 to 2.

2. The benzoguanamine compound having an amino methyl group, or a salt thereof according to claim 1, being o-aminomethylbenzoguanamine, m-aminomethylbenzoguanamine, or p-aminomethylbenzoguanamine, or a salt thereof.

3. A method for manufacturing a benzoguanamine compound having an amino methyl group, or a salt thereof comprising:

a reduction step for obtaining the benzoguanamine compound represented by the following Formula (1) having an aminomethyl group, or a salt thereof by hydrogen reduction of a cyanobenzoguanamine compound represented by the following Formula (2), or a salt thereof in the presence of a catalyst and a solvent:

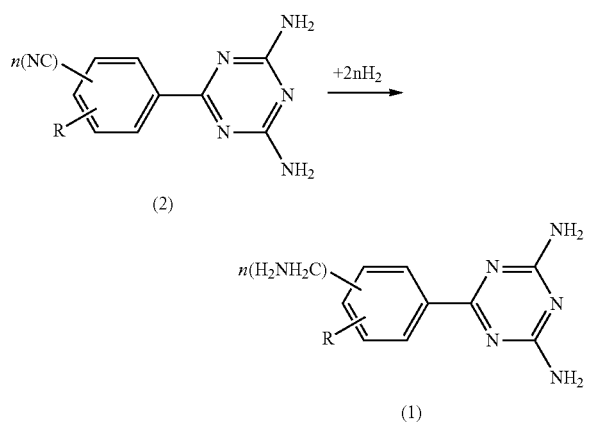

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.

4. The method for manufacturing the benzoguanamine compound having an amino methyl group, or a salt thereof according to claim 3, wherein the catalyst comprises a sponge metal catalyst.

5. A method for manufacturing a benzoguanamine compound having an amino methyl group, or a salt thereof comprising:

a reaction step for obtaining the benzoguanamine compound represented by the following Formula (1) having an aminomethyl group by reacting an aminomethylbenzonitrile compound represented by the following Formula (3), or a salt thereof with a dicyandiamide compound represented by the following Formula (4) or a salt thereof:

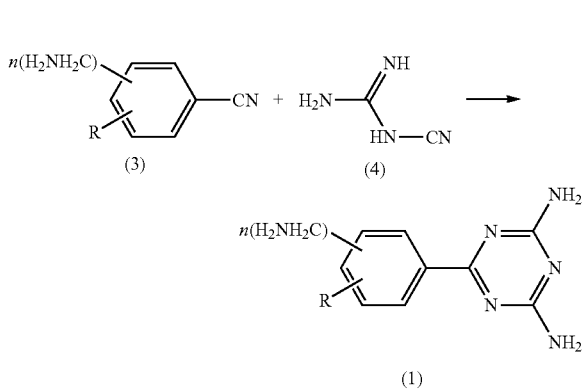

wherein R represents a substituent selected from the group consisting of hydrogen, an alkyl group having 1 to 10 carbon atoms, an alkoxy group having 1 to 10 carbon atoms, an aryl group having 6 to 10 carbon atoms, an aryloxy group having 6 to 10 carbon atoms, a hydroxyl group, an amide group, and a halogen atom; and n is an integer of 1 to 2.

* * * * *